United States Patent [19]

Causland et al.

[11] 4,369,173

[45] Jan. 18, 1983

[54] ANTIPERSPIRANT COMPOSITIONS

[75] Inventors: Robert H. Causland, Goshen; Americo V. Calogero, New Hampton, both of N.Y.

[73] Assignee: Wickhen Products, Inc., Huguenot, N.Y.

[21] Appl. No.: 21,835

[22] Filed: Mar. 19, 1979

Related U.S. Application Data

[63] Continuation-in-part of Ser. No. 527,841, Nov. 27, 1974, abandoned.

[51] Int. Cl.³ .............. A61K 9/36; A61K 9/62; A61K 7/38
[52] U.S. Cl. .................. 424/35; 424/DIG. 5; 424/47; 424/66; 424/67; 424/68; 424/69; 252/316
[58] Field of Search ................. 424/65, 68, 35; 252/316

[56] References Cited

U.S. PATENT DOCUMENTS

| | | | |
|---|---|---|---|
| 2,854,382 | 9/1958 | Grad | 424/68 |
| 2,996,431 | 8/1961 | Barry | 424/35 X |
| 3,011,949 | 12/1961 | Bilotti | 424/35 |
| 3,091,567 | 5/1963 | Wurzburg et al. | 424/35 |
| 3,096,248 | 7/1963 | Rudzki | 424/35 X |
| 3,116,206 | 12/1963 | Brynko et al. | 252/316 |
| 3,140,184 | 7/1964 | Robbins | 424/65 |
| 3,267,091 | 8/1966 | Denison | 424/65 X |
| 3,300,387 | 1/1967 | Kole | 424/68 X |
| 3,342,732 | 9/1967 | Goetz | 252/316 X |
| 3,383,307 | 5/1968 | Goetz | 252/316 |
| 3,407,254 | 10/1968 | Siegal et al. | 424/66 |
| 3,619,842 | 11/1971 | Maierson | 252/316 |
| 3,645,911 | 2/1972 | van Besauw | 252/316 |
| 3,660,115 | 5/1972 | Revie | 252/522 X |
| 3,691,271 | 9/1972 | Charle et al. | 252/522 X |
| 3,803,045 | 4/1974 | Matsukawa et al. | 252/316 |
| 3,812,056 | 5/1974 | Torriente et al. | 252/316 |
| 3,816,331 | 6/1974 | Brown, Jr. et al. | 252/316 |
| 3,819,838 | 6/1974 | Smith et al. | 252/316 |
| 3,829,412 | 8/1974 | Kunz | 252/316 |
| 3,886,085 | 5/1975 | Kiritani et al. | 252/316 |
| 3,893,933 | 7/1975 | Brown | 252/316 X |
| 3,971,852 | 7/1976 | Brenner et al. | 252/316 |
| 4,059,458 | 11/1977 | Germino et al. | 252/316 |
| 4,078,051 | 3/1978 | Pomot et al. | 424/35 |
| 4,080,039 | 3/1978 | Pomot | 424/46 |
| 4,080,438 | 3/1978 | Pomot | 424/68 |
| 4,100,103 | 7/1978 | Foris et al. | 252/316 |

FOREIGN PATENT DOCUMENTS

| | | | |
|---|---|---|---|
| 725594 | 1/1966 | Canada | 252/316 |
| 1000569 | 1/1957 | Fed. Rep. of Germany | 427/35 |
| 40-26918 | 11/1965 | Japan | 424/35 |
| 45-12759 | 9/1970 | Japan | 424/35 |
| 45-28390 | 9/1970 | Japan | 424/35 |
| 47-14726 | 5/1972 | Japan | 252/316 |
| 49-31816 | 3/1974 | Japan | 424/35 |

OTHER PUBLICATIONS

Zahejsky et al., J. Soc. Cosm. Chemists, 1972, vol. 23, pp. 775-789.
Miles et al., J. Soc. Cosmet. Chem., 1971, vol. 22, pp. 655-666.

Primary Examiner—Dale R. Ore
Attorney, Agent, or Firm—Steele, Gould & Fried

[57] ABSTRACT

Dry powder antiperspirant compositions consisting essentially of known active antiperspirant chemicals encapsulated and buffered with about 10 to about 45 percent, by weight, of the total composition of a hydrolyzed carbohydrate derived from natural waxy maize; a method of buffering active antiperspirant chemicals during processing to prevent corrosion of the processing equipment; aqueous solutions and gels capable of being dried to form the dry powder antiperspirant compositions; and antiperspirant consumer products formulated from the dry powders, are described.

29 Claims, No Drawings

ANTIPERSPIRANT COMPOSITIONS

This application is a continuation-in-part of application Ser. No. 527,841 filed Nov. 27, 1974 now abandoned.

BACKGROUND OF THE INVENTION

As is well-known in the art, effective antiperspirant chemicals are almost without exception acidic materials and, in general, the greater their acidity the greater their effectiveness as antiperspirants. The acidity of such materials, particularly that of the most highly acidic and effective materials such as aluminum chloride, raises a number of problems, among which may be mentioned corrosion of processing equipment, irritation of the skin of the user, and reduction of the tensile strength of fabrics in clothes worn by the user. Moreover, although aluminum chloride would be the preferred antiperspirant material because of its high antiperspirant activity, the utility of this material is severely limited by the difficulty of handling it in the anhydrous state in which it combines with water with explosive violence releasing great quantities of heat. For this reason, it has not been possible to use anhydrous aluminum chloride itself in the formulation of antiperspirant products. Therefore, it has been necessary heretofore to employ only aqueous solutions of this highly desirable antiperspirant chemical. While attempts have been made to remove the water from aqueous solutions of aluminum chloride to provide a dry powder material, none has been successful previously. When high heat has been used for this purpose, the aluminum chloride has been changed chemically to form aluminum oxide which is relatively ineffective as an antiperspirant. Attempts to avoid such oxidation of the aluminum chloride by the use of low heat in the drying of aqueous solutions of the chemical have also failed since the products have not been free-flowing readily utilizable powders. Moreover, since aqueous aluminum chloride has a pH of about 0.8, it is so acidic that it causes very serious corrosion problems.

Aqueous solutions of aluminum chlorhydrate, another commonly used antiperspirant chemical, have a pH of about 4.3 and are, therefore, much less corrosive, but this material is also less effective as an antiperspirant. It is recognized, however, that the antiperspirant activity of aluminum chlorohydrate can be increased by decreasing the proportion of aluminum to chlorine in the composition. Therefore, aluminum chlorhydrate compositions containing varying ratios of aluminum to chlorine are commercially available. In these compositions, as the proportion of aluminum to chlorine decreases from the 2:1 ratio found in aluminum chlorhydrate to the 1:3 ratio found in pure aluminum chloride, the effectiveness of the material as an antiperspirant is increased. However, the acidity of the material also increases and consequently the products become more difficult to manufacture due to corrosion normally attendant to the processing of such acidic materials. Many other astringent chemicals and combinations of chemicals useful as antiperspirants are known to the prior art. Among these, one of the best is zirconium hydroxychloride. This material, which has a pH of 1 or less, is also extremely difficult to process because of its corrosive nature.

Due to the acidity of the foregoing and other effective antiperspirant chemicals, it has been proposed to mix these materials with less acidic chemicals to achieve antiperspirant compositions which are effective but less corrosive and irritating than the unblended zirconium and aluminum salts.

The Prior Art

The prior art contains many references to the efficacy of antiperspirants of aluminum and zirconium salts and their modifications, among which may be mentioned an article entitled "A Comparison of the Effectiveness of Several External Antiperspirants", which appeared in the Journal of the Society of Cosmetic Chemists, Volume 23, No. 12, November 1972. Also of interest is Grad U.S. Pat. No. 2,854,382, issued Sept. 30, 1959, which discusses attempts of the prior art to buffer the strongly acid salts of aluminum, such as the sulfate and chloride, to reduce their acidity. This reference notes, however, that such buffering tends to reduce the efficacy of these materials as antiperspirants in line with the general rule that decreasing acidity is accompanied by decreasing antiperspirant activity. The Grad patent specifically discloses antiperspirant compositions comprising an aqueous solution of zirconyl hydroxychloride, an aluminum chlorhydroxide complex which acts as a buffer, an amino acid which also acts as a buffer, and an anti-gelling agent. The anti-gelling agent is necessitated by the fact that such combinations of strongly acid salts tend to gel, thus making them difficult to handle or dry to readily handleable powder form.

Also of interest is Siegal et al U.S. Pat. No. 3,407,254 issued Oct. 22, 1968 which notes that a variety of zirconium compounds have been suggested in the prior art for use as perspiration retarding or inhibiting compositions, but that in general most of these materials have been either too acid in character or too low in activity, as in the case with neutralized zirconium lactate and zirconium carbonate, for example. Siegal et al also note that it has been suggested that zirconium salts of monobasic mineral acids be used together with basic aluminum chloride, either alone or with an added buffering agent such as urea or glycine. The invention of the Siegal et al patent, however, involves a combination of a zirconium salt with a nucleophilic compound and an amino acid or an amino acid derivative. Such combinations of materials are said to form Werner type complexes which include zirconium, nucleophilic compound and amino acid compound. The nucleophilic compounds are described as electron dense species which tend to seek, find and stay near a cationic site. Suitable nucleophilic compounds include materials such as propylenediamine, triethyleneamine, diethylamine, monoethylamine and the like.

As noted above, it has been suggested that some of the problems associated with highly acidic antiperspirant chemicals might be ameliorated by the use of buffering agents. Another approach would be to use a binding agent which would release the strongly acid active compounds over a prolonged period of time. Robbins U.S. Pat. No. 3,140,184 issued July 7, 1964, while not dealing with antiperspirants, is of interest since it suggests that food substances can be complexed with cyclic dextrins which are believed to physically envelope the included molecules of organic compounds to be protected.

Denison U.S. Pat. No. 3,267,091 issued August 16, 1966, describes a process for forming a complex of boric acid with a hydroxy organic compound containing no more than twelve carbon atoms selected from the group consisting of unsubstituted polyhydroxy alkyl alcohols, hydroxy alkyl acids, polyhydroxy aromatics and hydroxy aromatic acids, and then reacting the resulting boric acid complex with a lower aluminum alkoxide. These materials are disclosed to have mild antiseptic, antiperspirant or astringent properties. The patent discloses glycerol, mannitol, gluconic acid, glycolic acid, lactic acid, malic acid, tartaric acid, citric acid, salicylic acid, ethylene glycol, sucrose, gallic acid, pyrogallol and pyrocatechol as suitable hydroxy compounds for use in these boric acid complexes.

Kole U.S. Pat. No. 3,300,387 issued Jan. 24, 1967, relates to topically applied antiperspirant products in the form of a pressed powder containing a hygroscopic active ingredient. In these products finely divided particles of active antiperspirant chemical are coated with a water soluble substantially non-hygroscopic wax-like material and then mixed with an inert powder base or carrier, if desired, and formed into a pressed powder cosmetic or pharmaceutical product for application to the skin. The antiperspirant chemicals may be aluminum chlorhydrate, sodium aluminum lactate complex, sodium zirconium lactate complex, aluminum sulfate or the like. The wax-like material must be water soluble or water dispersible at human body temperature so it will disintegrate by body perspiration and release the antiperspirant, and in addition, it should be soluble in a non-aqueous solvent so that it can be applied to the hygroscopic material in the form of a non-aqueous solution. Suitable wax-like products are disclosed to be polyethylene glycols having an average molecular weight in the range from 1000 to 6000, such as "Polyglycol 1000" (Dow Chemical); "Carbowax 1500" and "Carbowax 4000" (Carbide and Carbon Chemical Company); polypropylene glycols having an average molecular weight in the range from 140 to 600; methoxy polyethylene glycols having an average molecular weight of 350 to 750; ethoxylated fatty acids and alcohols containing 8 to 20 carbon atoms; fatty acid esters of polyalcohols where the fatty chain contains 8 to 20 carbon atoms; ethoxylated lanolin; and lanolin extracts and fractions. The coating operation is carried out by dissolving the wax-like material in a non-aqueous solvent, mixing in the antiperspirant particles and then evaporating the solvent by suitable means such as tray drying and spray drying. It is said that the solvent should be substantially anhydrous and volatile, and should not dissolve the antiperspirant. Suitable solvents include isopropyl alcohol, ethyl alcohol, methyl alcohol, dichloroethyl ether, trichloroethylene, ethyl acetate, dimethyl phthalate, toluene and the like.

From the foregoing it should be apparent that a wide variety of antiperspirant chemicals are known to the art including single active compounds, mixtures of active compounds and compositions containing either single or mixed antiperspirant chemicals together with buffering, anti-gelling and other agents intended to mitigate the problems long associated with the manufacture and use of such materials. However, a need still exists in the art for a method and means for reducing the corrosion of equipment during processing of highly acid materials and for aqueous solutions of chemicals which do not gel during processing or which produce gels which nevertheless can be dried to produce free flowing powders. There also remains a need for dry powder antiperspirant compositions which can be readily formulated to provide prolonged antiperspirant activity at a pH which does not irritate the user's skin or damage his clothing.

It is, therefore, a primary object of the invention to provide a method for reducing the corrosion of processing equipment previously attendant upon the manufacture of antiperspirant chemicals.

It is another object of the invention to provide aqueous solutions of antiperspirant chemicals which do not corrode processing equipment, and either do not gel during the time required to process them or which produce gels capable of being dried to free-flowing powders by available techniques.

It is still another object of the invention to provide free-flowing dry powder antiperspirant compositions in which the active antiperspirant chemical is encapsulated in a material which buffers the composition to a pH acceptable from the point of view of irritation of the skin of the user and deterioration of fabrics.

It is yet another object of the invention to provide antiperspirant compositions and formulations from which the active antiperspirant chemical is released slowly over a prolonged period of time to provide long-lasting antiperspirant activity.

It is another object of the invention to provide dry powder antiperspirant compositions which are easily and conveniently formulated into a wide variety of consumer products such as creams, sticks, roll-ons, powders, aerosols and the like.

It is still another more specific object of the invention to produce highly acidic antiperspirant chemicals which are encapsulated in such a way as to inhibit their corrosive action on processing equipment and their tendency to degrade the tensile strength of fibers in the clothing of the user.

It is another object of the invention to buffer highly acidic antiperspirant chemicals through the function of an encapsulating medium to increase the pH thereof to a dermatogically acceptable level.

It is another object of the invention to reduce and/or control the hygroscopicity of antiperspirant chemicals by means of an encapsulating medium and to thus control the time of release of the active antiperspirant under use conditions.

It is another specific object of the invention to prevent or control gelation of aqueous solutions of mixtures of highly acidic antiperspirant chemicals, such as mixtures of aluminum and zirconium salts over a wide range of molecular proportions.

SUMMARY OF THE INVENTION

The foregoing and other objects of the invention, which will become apparent from the following disclosure, are achieved by providing aqueous solutions containing one or more active antiperspirant chemicals and one or more encapsulating agents. The water is then removed from these aqueous solutions by conventional means such as tray drying or, preferably, by spray drying, to form dry free-flowing antiperspirant compositions in which the active antiperspirant chemicals are encapsulated and buffered to permit formulation of consumer antiperspirant products which have a pH sufficiently high to be dermatogically acceptable and to substantially avoid damage to the clothing of the user. The encapsulating agents of the invention serve not only to buffer the aqueous solutions so as to reduce corrosion of the processing equipment, but also to either prevent gelation of aqueous solutions of mixed highly acidic antiperspirant chemicals during processing or provide gels which are capable of being dried to produce a composition which can be transformed into a free-flowing powder. The encapsulating agents also control the hygroscopicity of the finished dry free-flowing antiperspirant compositions so that they do not absorb undue amounts of moisture from the atmosphere but utilize the moisture on the user's skin so as to release the active antiperspirant chemicals slowly, thus providing long-lasting antiperspirant activity for the consumer product.

The aqueous solutions and any gels which are formed therefrom contain about 25 to about 45 percent by weight of the total composition of one or more active antiperspirant chemicals and from about 3 to about 45 percent by weight of one or more of the encapsulating agents. The proportions of antiperspirant and encapsulating agent in such solutions should be such as to provide dry powders upon removal of water, which dry powders comprise about 3 to 45 percent, preferably 10 to 45 percent, of encapsulating agent and about 55 to 90 percent antiperspirant. These aqueous solutions, when dried by any suitable method such as spray drying, produce dry compositions which can be pulverized by conventional techniques to produce dry, free-flowing powders, suitable for formulation by conventional techniques into a wide variety of consumer antiperspirant products including but not limited to creams, sticks, roll-ons, powders, aerosol products and the like.

The encapsulating agents employed in the present invention are hydrolyzed carbohydrates and mixtures thereof derived from natural waxy maize. A simple test has been developed which indicates with a high degree of reliability the effectiveness of any particular hydrolyzed carbohydrate derived from natural waxy maize as an encapsulating agent for commercial use in the present invention. Among the limiting factors on the efficacy of the encapsulating agents are (1) the capability of dissolving in an aqueous solution containing the active antiperspirant chemicals to form a solution which (2) can be dried by conventional means to form a composition which can be pulverized to a dry powder adapted to be easily incorporated in a variety of consumer antiperspirant products. Therefore, an aqueous solution drying test serves to indicate the commercial feasability of encapsulating agents. A suitable standard test for this purpose is described below.

Standard Solution Drying Test

1. Prepare an antiperspirant composition in the form of an aqueous solution containing a known amount, e.g. from 10 to 45% by weight of the encapsulating agent to be tested, and for example, from 55 to 90% by weight of the active antiperspirant chemical, a particularly useful solution containing about 5% of an encapsulating agent and about 25% by weight, of antiperspirant chemical.

2. Place 5 standard drops of the test solution on a clean glass slide and spread the liquid evenly over the surface of the slide with a spatula or other suitable means.

3. Place the slide with the liquid-coated side up on a hot plate or other surface maintained at a temperature of about 350° to about 400° F. and record the time required to dry the liquid film.

4. Remove the slide from the heat and permit to cool to about room temperature, scrape the dry film from the slide with a suitable instrument and observe the physical nature of the scrapings.

The time required to dry the film may vary from as little as 15 seconds to as much as 10 minutes or more. It has been found that any potential encapsulating agent which gives a solution which dries in about 60 seconds or less under the above conditions to produce flaky or powdery scrapings, is operable in commercial use in the present invention, as by spray drying, tray drying or the like. It has also been observed that if the film requires as much as about 60 to 100 seconds to dry under these conditions, the encapsulating agent will be found to be generally undesirable on a commercial scale. When the time required to dry the film is in excess of approximately 100 seconds under these test conditions, the encapsulating agent is generally considered undesirable on a commercial scale since it has been observed that it is difficult or impossible to dry such solutions on a commercial scale as by spray drying, for example. Therefore, the foregoing small scale drying test provides a quick and reliable means for determining the extent to which any given potential encapsulating agent will be commercially operable in the invention to permit the drying of aqueous solutions of antiperspirant chemicals to a dry, pulverizable state to produce the novel encapsulated antiperspirant compositions of the invention.

As will be apparent to those skilled in the art, the foregoing standard test is only one of many similar tests that could be devised by trial and error to serve as a guide to commercial operability. The concentrations of encapsulating agent and antiperspirant chemical could be varied appropriately, generally within the aforementioned ranges, according to the commercial practice to be employed, so long as they are standardized for any series of tests and properly correlated to commercial operability by actual tests under plant scale conditions (see e.g. Table II below).

The at least partially hydrolyzed carbohydrates which are useful in the present invention are all capable of being dissolved in aqueous solutions of the antiperspirant chemicals to form solutions which can be conveniently processed in conventional equipment composed of stainless steel or other materials without the characteristic high degree of corrosion normally caused by aqueous solutions of highly acidic antiperspirants. In general, the hydrolyzed carbohydrates are dissolved in such solutions in concentrations of from about 3 percent up to about 55 percent by weight. The solutions normally contain from about 25 to about 45 percent by weight of the active antiperspirant chemical. However, as noted above, such solutions on removal of water should be in the form of a free flowing dry power containing about 3 to 45%, preferably 10 to 45% of encapsulating agent and 55 to 90% of antiperspirant chemical.

A wide variety of hydrolyzed carbohydrates derived from corn starch from natural waxy maize are available commercially and are commonly referred to as dextrin, malto-dextrin or corn syrup solids, depending upon the degree of conversion of the corn starch to hydrolyzed carbohydrate. The distribution of monosaccharides and polysaccharides in a typical product of this type are set forth in Table I below. In that table, Encapsulator A, which is a typical dextrin, is a white powder having a pH of 4.0 to 4.7 in a 20% aqueous solution. This material, as received, has a maximum moisture content of 5% but will absorb up to about 13% moisture and still remain a free flowing powder, although the material is relatively nonhygroscopic for a refined low-dextrose equivalent (9 to 12) product. This representative dextrin readily dissolves in water to form clear solutions of 35 to 40% concentration of the hydrolyzed carbohydrate. Similarly, Encapsulator G of Table I is a typical corn syrup solids product in the form of a white powder soluble in water to make a clear solution which has a pH of 4.8 to 5.2 at a concentration of 50% carbohydrate. The intermediately hydrolyzed products such as Encapsulator D of Table I are commonly referred to as malto-dextrin whose solubility is intermediate that of the less hydrolyzed and thus less soluble dextrins and the more hydrolyzed and thus more soluble corn syrup solids. Preferably, the at least partially hydrolyzed carbohydrates used in the invention have a solubility in water of the dextrins derived from waxy maize, i.e. at least about 35%, by weight.

TABLE I

DISTRIBUTION OF SACCHARIDES IN COMMERCIALLY AVAILABLE CARBOHYDRATE MIXTURES IN PERCENT BY WEIGHT

|  | Dextrose Equivalent | Dextrose | Disaccharides | Trisaccharides | Tetrasaccharides And Higher | Solution Characteristics |
|---|---|---|---|---|---|---|
| Encapsulator A (Maltrin 10)[a] | 9–12 | 0.5 | 3.5 | 6.5 | 89.5 | clear solution 34–40% solids |
| Encapsulator B (Maltrin 15) | 13–17 | 1.0 | 3.5 | 7.5 | 88.0 | clear solution 60% solids |
| Encapsulator C (Maltrin 20) | 18–22 | 1.0 | 6.0 | 8.0 | 85.0 | clear solution 70% solids |
| Encapsulator D (Maltrin 250) | 23–27 | 2.5 | 5.0 | 8.5 | 84.0 | clear solution 73% solids |
| Encapsulator E (Maltrin 300) | 28–32 | 3.0 | 9.0 | 9.0 | 79.0 | clear solution 75% solids |
| Encapsulator F (Maltrin 360) | 34–38 | 14.0 | 12.0 | 10.0 | 64.0 | clear solution 75% solids |
| Encapsulator G (Maltrin 36HM) or Dri-Sweet SS-35[b] | 34–38 | 6.0 | 29.0 | 11.0 | 54.0 | clear solution 75% solids |
| Encapsulator H (Maltrin 420) | 40–44 | 19.0 | 12.0 | 11.0 | 58.0 | clear solution 75% solids |
| Encapsulator I (Maltrin 425) | 40–44 | 7.0 | 39.0 | 17.0 | 37.0 | clear solution 75% solids |

[a]"Maltrin" is a trademark of Grain Processing Corporation of Muscatine, Iowa from which all of the "Maltrin" products listed are available.
[b]Manufactured by The Hubinger Company, Keokuk, Iowa.

The carbohydrate mixtures listed in Table I above were screened by the standard solution drying test described above, for utility in the invention. The results of these tests are set forth in Table II below.

TABLE II

RESULTS OF SCREENING TESTS TO DETERMINE THE DRYING CHARACTERISTICS OF AQUEOUS SOLUTIONS OF COMMERCIAL CARBOHYDRATE-MIXTURES

| Aqueous Compositions | Parts By Weight | Time To Dry | Condition Of Film | Liquid/ Gel | pH |
|---|---|---|---|---|---|
| Control |  |  |  |  |  |
| Aluminum Chlorhydrate[1] | 50.6 | 20 Sec. | Powdery | G | 3.50 |
| Zirconyl Chlorhydrate[2] | 30.4 |  |  |  |  |
| Aluminum Chloride[3] | 100.0 | 25 Sec. | Powdery | L | 2.00 |
| Aluminum Sulfate[4] | 100.0 | 25 Sec. | Powdery | L | 1.80 |
| Zirconyl Chlorhydrate | 100.0 | 25 Sec. | Powdery | L | 0.80 |
| Aluminum Chlorhydrate | 100.0 | 20 Sec. | Powdery | L | 4.20 |
| Aluminum Chlorhydrate | 50.6 | 15–18 Sec. | Flaky | G | — |
| Zirconyl Chlorhydrate | 30.4 |  |  |  |  |
| Encapsulator A | 18.9 |  |  |  |  |
| Aluminum Chlorhydrate | 50.6 | 15–18 Sec. | Powdery | G | 3.94 |
| Zirconyl Chlorhydrate | 30.4 |  |  |  |  |
| Encapsulator B | 18.9 |  |  |  |  |
| Aluminum Chlorhydrate | 50.6 | 15–18 Sec. | Powdery | L | 4.00 |
| Zirconyl Chlorhydrate | 30.4 |  |  |  |  |
| Encapsulator C | 18.9 |  |  |  |  |
| Aluminum Chlorhydrate | 50.6 | 15–18 Sec. | Powdery | L | 3.98 |
| Zirconyl Chlorhydrate | 30.4 |  |  |  |  |
| Encapsulator D | 18.9 |  |  |  |  |
| Aluminum Chlorhydrate | 50.6 | 15–18 Sec. | Powdery | L | 3.98 |
| Zirconyl Chlorhydrate | 30.4 |  |  |  |  |
| Encapsulator E | 18.9 |  |  |  |  |
| Aluminum Chlorhydrate | 50.6 | 15–18 Sec. | Powdery | L | 3.98 |
| Zirconyl Chlorhydrate | 30.4 |  |  |  |  |
| Encapsulator F | 18.9 |  |  |  |  |
| Aluminum Chlorhydrate | 50.6 | 15–18 Sec. | Powdery | L | 4.00 |
| Zirconyl Chlorhydrate | 30.4 |  |  |  |  |
| Encapsulator G | 18.9 |  |  |  |  |
| Aluminum Chlorhydrate | 50.6 | 15–18 Sec. | Powdery | L | 3.98 |
| Zirconyl Chlorhydrate | 30.4 |  |  |  |  |
| Encapsulator H | 18.9 |  |  |  |  |
| Aluminum Chlorhydrate | 50.6 | 15–18 Sec. | Powdery | L | 3.95 |
| Zirconyl Chlorhydrate | 30.4 |  |  |  |  |
| Encapsulator I | 18.9 |  |  |  |  |
| Aluminum Chloride | 50 | 35 Sec. | Flaky | L | 2.85 |
| Encapsulator B | 10 |  |  |  |  |

TABLE II-continued
RESULTS OF SCREENING TESTS TO DETERMINE THE DRYING CHARACTERISTICS OF AQUEOUS SOLUTIONS OF COMMERCIAL CARBOHYDRATE-MIXTURES

| Aqueous Compositions | Parts By Weight | Time To Dry | Condition Of Film | Liquid/ Gel | pH |
|---|---|---|---|---|---|
| Water | 10 | | | | |
| Aluminum Chloride | 50 | 25 Sec. | Flaky | L | 2.90 |
| Encapsulator G | 10 | | | | |
| Water | 10 | | | | |
| Aluminum Sulfate | 50 | 30 Sec. | Powdery | L | 3.20 |
| Encapsulator B | 10 | | | | |
| Water | 10 | | | | |
| Aluminum Sulfate | 50 | 30 Sec. | Powdery | L | 3.50 |
| Encapsulator G | 10 | | | | |
| Water | 10 | | | | |
| Aluminum Chlorhydrate | 30 | 15 Sec. | Powdery | L | 4.15 |
| Aluminum Chloride | 10 | | | | |
| Encapsulator B | 4.4 | | | | |
| Aluminum Chlorhydrate | 30 | 15 Sec. | Powdery | L | 4.35 |
| Aluminum Chloride | 10 | | | | |
| Encapsulator G | 4.4 | | | | |
| Aluminum Bromohydrate Solution | 10 | 40 Sec. | Powdery | L | 3.19 |
| Encapsulator G | 1 | | | | |
| Aluminum Iodohydrate Solution | 10 | 60 Sec. | Powdery | L | 3.55 |
| Encapsdulator G | 1 | | | | |

(1)The aluminum chlorhydrate employed was a 50% aqueous solution in all cases.
(2)The zirconyl chlorhydrate employed was a 20% aqueous solution in all cases.
(3)The aluminum chloride employed was a 50% aqueous solution.
(4)The aluminum sulfate employed was a 25% aqueous solution.
(5)The aluminum bromohydrate and iodohydrate employed were 50% aqueous solutions.

It should be noted that for purpose of comparison, various mixtures of antiperspirant materials containing aluminum chlorhydrate and zirconium chlorhydrate were included in the foregoing battery of tests. It has been found that the results set forth in Table II above are representative and typical of those obtained with a wide variety of single and mixed antiperspirant chemicals.

As noted above, the provision of buffering is an important consideration for antiperspirant formulations, and a major advantage of the compositions of the present invention. It has been discovered that all of the carbohydrate materials used in the present invention exhibit a modifying affect on the acidic nature of all known antiperspirant chemicals. As shown in Table II, the acidity of the active antiperspirant chemicals, as measured by a change in pH is consistently decreased by the use of the carbohydrate encapsulators, which indicate uniform and highly desirable buffering action directly related to the presence of these encapsulators.

It should be noted that the amounts of the ingredients are expressed in parts by weight in Table II and elsewhere herein since this is usual in the art and reflects the amounts of the commercially available products used. It should be recognized that such amounts cna be easily converted to percentages of the dry solid ingredients by weight of the total composition, whether it is a solution or a dry powder, by simple arithmetical calculation. For example, many of the solutions set forth in Table II are 50.6 parts by weight of a 50% aqueous solution of aluminum chlorhydrate, 30.4 parts by weight of 20% aqueous solution of zirconyl chlorhydrate, and 18.9 parts by weight of one of the encapsulators A through I. It can be seen, therefore, that such solutions contain 25.3 parts of dry aluminum chlorhydrate, about 6.1 parts of dry zirconyl chlorhydrate and 18.9 parts of dry encapsulator for a total solids content of 50.3 parts by weight; the remaining 49.3 parts by weight being water. Inasmuch as the total parts by weight are approximately equivalent to percentages by weight, i.e., the solutions contain about 25.3% aluminum chlorhydrate, about 6.1% zirconyl chlorhydrate and about 49.3% water. Therefore, the total antiperspirant content is about 31.5%; the encapsulator content is about 19% and the water content is about 49.5%, by weight of the total solutions. It should also be obvious that after removal of the water by spray drying or other suitable means, the dry powder compositions contain about 62.5% antiperspirant and about 37.5% encapsulating agent.

Similarly, other solutions in Table II which are made up of 50 parts by weight of 50% aqueous aluminum chloride solution, 10 parts by weight of additional water and 10 parts by weight of dry encapsulator B or G, can be calculated to contain the following percentages of dry antiperspirant and encapsulator based on the weight of the total solution: Aluminum chloride, about 35.7%; encapsulator, about 14.3%; the remainder of about 50.0% being water. The dry powder obtained from such solutions contains about 71% aluminum chloride and about 29% encapsulator.

In the solutions made up from 50 parts by weight of 25% aqueous aluminum sulfate, 10 parts of dry encapsulator and 10 parts of added water, the ingredients are present in the solution in the following percentages by weight: aluminum sulfate, about 17.9%; encapsulator B or G, about 14.3%; the remainder, about 67.8% being water. The dry powder obtained from such a solution contains about 55.5% aluminum sulfate and about 44.5% encapsulator.

In the solutions made up from 30 parts by weight of 50% aqueous aluminum chlorhydrate, 10 parts by weight of 50% aqueous aluminum chloride solution and 4.4 parts by weight of dry encapsulator B or G, the percentage composition is as follows: about 33.9% aluminum chlorhydrate; about 11.3% aluminum chloride; about 10% encapsulator; the remaining 44.8% being water. This produces on drying, a powdered composition containing, although in altered form, about 61.5% aluminum chlorhydrate, about 20.5% aluminum chloride and about 18.0% encapsulator.

In the solutions of Table II containing 10 parts by weight of 50% aqueous aluminum bromohydrate or iodohydrate solution and 1 part by weight of Encapsulator G, the percentage composition of the solution is about 45.5% aluminum salt; about 9% encapsulator; the remainder, about 45.5% being water. Such solutions, on drying, produce powders containing about 83.3% aluminum salt and about 16.7% encapsulator.

The term "hydrolyzed carbohyrate" as used herein is intended to mean that the encapsulating material is sufficiently hydrolyzed to provide an aqueous solution thereof containing at least about 35% solids by weight of the solution. Starch, itself, is insoluble or only very slightly soluble, but on hydrolysis its solubility increases dramatically, thus providing material useful in the invention. It is, of course, preferred that the encapsulating materials be soluble to a greater degree than 35% and, indeed, solubilities of as much as 75% are desirable. As noted above, the encapsulators are used in the aqueous solutions, with dissolved antiperspirant chemicals, in concentrations as high as about 55% by weight.

General Procedure For Encapsulating Antiperspirant Chemicals With Carbohydrate Encapsulators As explained above, the glass slide screening test was developed to determine the suitability of aqueous solutions of encapsulating media and antiperspirant chemicals for being dehydrated to form dry powder antiperspirant compositions under commercial conditions. In order to confirm the indications of the glass slide screening tests in actual practice, a pilot model spray drier (Komline-Sanderson "Little Giant" Drier) was employed. This drier consists of a cylindrical chamber about $3\frac{1}{4}'$ in diameter, and about 3' high, having a conical bottom section (approximately 60°) extending approximately 3' below the straight upright side. A multifluid conventional liquid atomizer was used to introduce the solutions to be dried to the spray drying apparatus. The general processing conditions used for all of the aqueous encapsulator-antiperspirant solutions were as follows:

| | |
|---|---|
| Inlet Temperature | 300–450° F. |
| Outlet Temperature | 175–250° F. |
| Air Pressure | 65–95 psi |
| Feed Rate Range | 50 milliliters per minute to 200 milliliters per minute |
| Temperature of Test Solutions | Ambient |
| Viscosity of Test Solutions | Less than 2,000 cps |

These conditions may, of course, be varied according to the knowledge of the prior art of spray drying. It should also be recognized that other conditions known to the art may be employed which are appropriate for drying of such solutions by other known methods of water removal such as drum drying, tray drying, and so forth.

SPRAY DRYING TESTS

Example I

Aluminum Sulfate

| Components | Parts by Weight | |
|---|---|---|
| $Al_2(SO_4)_3 \cdot 14H_2O$ | 14 | 18.2 |
| Water | 56 | 72.7 |
| Encapsulator G | — | 9.1 |
| pH of 10% Solution | 2.5 | 3.5 |

The aluminum sulfate and the encapsulator were solubilized in the amounts of water specified above. No gel formed in either case. The resulting solutions were spray dried by the general procedure set forth above to obtain a fine powder in each case. During the spray drying operation, the solution containing no encapsulator was observed to visibly corrode the interior wall of the drier chamber and the interior of the pump used to feed the drier. In the case of the second solution containing the encapsulator, no evidence of corrosion was observed in either the drier or pump.

Example 2

Aluminum Chloride

| Components | Parts by Weight | |
|---|---|---|
| $AlCl_3 \cdot 6H_2O$ (50% Solution) | 100 | 50.00 |
| Encapsulator G | — | 10.0 |
| Water | — | — |
| pH of 10% Solution | 2.8 | 3.2 |

After making up the indicated aqueous solutions, they were spray dried according to the above general procedure. During the spray drying operation there was evidence of corrosive activity by the aluminum chloride solution on the apparatus and it was also noted that the antiperspirant chemical was degraded since very strong hydrochloric acid fumes were released. On the other hand, practically no evidence of hydrochloric acid fumes was noted and there was no evidence of corrosion in the equipment during the spray drying of the solution containing the encapsulator.

Example 3

Aluminum Chlorhydrate

| Components | Parts by Weight | |
|---|---|---|
| $Al_2(OH)_5Cl \cdot xH_2O$ (50% Solution) | 100 | 85 |
| Encapsulator G | — | 15 |
| Water | — | — |
| pH of 10% Solution | 4.2 | 4.35 |

During this test, which was conducted in the same way, very small quantities of hydrochloric acid fumes were noted in the solution without the encapsulator, and no fumes were observable with the encapsulator present. There was no evidence of corrosive activity for either test solution.

Example 4

Zinc Phenolsulfonate

| Components | Parts By Weight | |
|---|---|---|
| $Zn(HOC_6H_4SO_3)_2 \cdot 8H_2O$ | 10.0 | 18.2 |
| Encapsulator G | — | 9.1 |
| Water | 90.0 | 72.7 |
| pH of 10% Solution | 4.6 | 5.3 |

Zinc phenolsulfonate is commercially available as a powder. The test solution above was spray dried with no apparent problems of molecular degradation or corrosion.

Additional spray drying tests were conducted employing blends of more than one type of antiperspirant chemical to show that the encapsulators of the invention are also effective when more than one antiperspirant chemical is present; thus demonstrating further the versatility of the invention. The following spray drying tests are typical of such practice.

Example 5

Aluminum Chlorhydrate And Aluminum Chloride

| Components | Parts | Dry Basis |
|---|---|---|
| Aluminum Chlorhydrate (50% Solution) | 67.6 | 33.8 |
| $AlCl_3.6H_2O$ (50% Solution) | 22.5 | 11.3 |
| Encapsulator G | 9.9 | 9.9 |

Example 6

Aluminum Chlorhydrate And Aluminum Chloride

| Components | Parts | Dry Basis |
|---|---|---|
| Aluminum Chlorhydrate (50% Solution) | 59.1 | 29.5 |
| $AlCl_3.6H_2O$ (50% Solution) | 31.8 | 15.9 |
| Encapsulator G | 9.1 | 9.1 |

To further illustrate that the encapsulators of this invention do not interfere with other additives that have been used as buffering agents in the past, mixtures of antiperspirant chemicals and these encapsulators in the presence of other buffering agents such as urea and aminoacetic acid were spray dried according to the general procedure described above as follows:

EXAMPLE 7

| Components | Parts | Dry Basis |
|---|---|---|
| Aluminum Chlorhydrate (50% Solution) | 40.2 | 20.1 |
| Zirconium Chlorhydrate (20% Solution) | 48.2 | 9.6 |
| Encapsulator G | 10.1 | 10.1 |
| Aminoacetic Acid | 1.5 | 1.5 |

EXAMPLE 8

| Components | Parts | Dry Basis |
|---|---|---|
| Aluminum Chlorhydrate (50% Solution) | 35.8 | 17.9 |
| Zirconium Chlorhydrate (20% Solution) | 57.3 | 11.5 |
| Encapsulator G | 6.0 | 6.0 |
| Aminoacetic Acid | 0.9 | 0.9 |

EXAMPLE 9

| Components | Parts | Dry Basis |
|---|---|---|
| Aluminum Chlorhydrate (50% Solution) | 70.0 | 35.0 |
| Zirconium Chlorhydrate (20% Solution) | 22.0 | 4.4 |
| Encapsulator G | 6.0 | 6.0 |
| Urea | 2.0 | 2.0 |

No gelling was observed in the aqueous compositions of Examples 5 through 9 and all of these solutions were successfully spray dried and micronized to provide dry impalpable powders.

Not unexpectedly, not all of the encapsulators are equally desirable. For example, some are less able to prevent gelling than others as the antiperspirant solutions become more strongly acidic, e.g., encapsulators A and the variation in gel preventing characteristics of some of the operable encapsulators is illustrated in highly acidic antiperspirant solutions in Table III below.

TABLE III

VARIATION IN GELLING CHARACTERISTICS OF SOLUTIONS OF SOME HIGHLY ACIDIC ANTIPERSPIRANT COMPOSITIONS IN THE PRESENCE OF CERTAIN ENCAPSULATING AGENTS

| | Control | Parts By Weight | | | |
|---|---|---|---|---|---|
| | | 1 | 2 | 3 | 4 |
| Series A | | | | | |
| Aluminum Chlorhydrate (1) | 28.5 | 26.3 | 26.3 | 26.3 | 26.3 |
| Zirconyl Chlorhydrate (2) | 71.5 | 65.8 | 65.8 | 65.8 | 65.8 |
| Encapsulator G | — | 7.9 | — | — | — |
| Encapsulator I | — | — | 7.9 | — | — |
| Encapsulator A | — | — | — | 7.9 | — |
| Liquid/Gel | G | L | Semi G | G | G |
| Time to Gel (approximate) | 1 Hr. | | 4 Hrs. | 15 Mins. | 10 Min. |
| Series B | | | | | |
| Aluminum Chlorhydrate (1) | 16.7 | 15.4 | 15.4 | 15.4 | 15.4 |
| Zirconyl Chlorhydrate (2) | 83.3 | 76.0 | 76.0 | 76.0 | 76.0 |
| Encapsulator G | — | 7.6 | — | — | — |
| Encapsulator I | — | — | 7.6 | — | — |
| Encapsulator A | — | — | — | 7.6 | — |
| Liquid/Gel | G | G | G | G | G |
| Time to Gel (approximate) | 1 Hr. | 1 Hr. | 2 Hrs. | 1 Hr. | 1 Hr. |

(1) 50% aqueous solution.
(2) 20% aqueous solution.

The ability of the encapsulators proposed according to this invention to inhibit gelling of highly acid aqueous antiperspirant solutions depends not only upon the identity of the enscapsulating agent, but upon its concentration in the solutions. It has been found that concentrations as low as about 3%, by weight of the solution provide a marked degree of inhibition of gelling and that concentrations as high as about 45% by weight may be employed for this purpose. In general, however, it has been found that adequate inhibition of gelling is obtained employing about 10 to 20% of the carbohydrate, by weight of the solution to be stabilized.

To demonstrate the differences in gelling time as well as to show once again the consistent buffering effect of the encapsulators, the effect of the encapsulator concentration on varying blends of antiperspirant chemicals is shown in Tables IV, V and VI. In the case of Table IV a blend of aluminum chlorhydrate and zirconyl chlorhydrate in a ratio of 4:1 (by weight of the chemicals) was investigated over a wide range of Encapsulator G concentrations. For this 4:1 ratio, it was found that the most desirable concentration of this encapsulator lies in the range of about 10% to about 20% by weight of the solution.

TABLE IV
EFFECT OF VARIOUS CONCENTRATIONS OF ENCAPSULATOR G ON THE GELLING TIME OF AQUEOUS SOLUTIONS CONTAINING ALUMINUM CHLORHYDRATE AND ZIRCONYL CHLORHYDRATE IN A WEIGHT RATIO OF 4:1 ON AN ANHYDROUS BASIS

| | Control | Parts By Weight | | | | | | | | |
| | | 1 | 2 | 3 | 4 | 5 | 6 | 7 | 8 | 9 |
|---|---|---|---|---|---|---|---|---|---|---|
| Aluminum Chlorhydrate (1) | 59.7 | 59.7 | 57.9 | 55.9 | 54.1 | 52.3 | 50.6 | 49.1 | 47.6 | 46.2 |
| Zirconyl Chlorhydrate (2) | 39.8 | 35.8 | 34.8 | 33.6 | 32.4 | 31.7 | 30.4 | 29.5 | 28.6 | 27.8 |
| Encapsulator G | — | 4.5 | 7.3 | 10.5 | 13.5 | 16.3 | 18.9 | 21.4 | 23.8 | 26.0 |
| Liquid/Gel | G | G | G | G | G | G | L | L | L | L |
| Time to Gel (Approximate/Minutes) | 10 | 30 | 35 | 40 | 45 | 60 | — | — | — | — |
| pH of 10% solution | 3.2 | 3.6 | 3.7 | 3.7 | 3.8 | 3.9 | 4.0 | 4.0 | 4.0 | 4.0 |

(1) 50% aqueous solution.
(2) 20% aqueous solution.

In another series of tests a blend of aluminum chlorhydrate and zirconyl chlorhydrate in a ratio of 3:1 (anhydrous basis) was investigated over a wide range of Encapsulator G concentrations, and it was found that the most desirable concentration of this encapsulator in such compositions was in the range of about 7 to about 19% by weight of the solution.

TABLE V
EFFECT OF VARIOUS CONCENTRATIONS OF ENCAPSULATOR G ON THE GELLING TIME OF AQUEOUS SOLUTIONS CONTAINING ALUMINUM CHLORHYDRATE AND ZIRCONYL CHLORHYDRATE IN A WEIGHT RATIO OF 3:1 ON AN ANHYDROUS BASIS

| | Control | Parts By Weight | | | | |
| | | 1 | 2 | 3 | 4 | 5 |
|---|---|---|---|---|---|---|
| Aluminum Chlorhydrate (1) | 51.7 | 51.7 | 59.2 | 46.9 | 44.8 | 42.9 |
| Zirconyl Chlorhydrate (2) | 43.1 | 43.1 | 41.0 | 39.1 | 37.3 | 35.7 |
| Encapsulator G | — | 5.1 | 9.8 | 14.1 | 18.9 | 21.4 |
| Liquid/Gel | G | G | G | G | L | L |
| Time to Gel (Approximate) | 10 Mins. | 35 Mins. | 50 Mins. | 4 Hrs. | — | — |
| pH of 10% Solution | 3.2 | 3.7 | 3.8 | 3.8 | 3.8 | 3.9 |

(1) 50% aqueous solution.
(2) 20% aqueous solution.

In still another series of tests a blend of aluminum chlorhydrate and zirconyl chlorhydrate in a ratio of 2:1 on an anhydrous basis was investigated over a wide range of Encapsulator G concentrations, and it was found that the most desirable concentrations are in the range of about 12% to about 22% for these solutions.

TABLE VI
EFFECT OF VARIOUS CONCENTRATIONS OF ENCAPSULATOR G ON THE GELLING TIME OF AQUEOUS SOLUTIONS CONTAINING ALUMINUM CHLORHYDRATE AND ZIRCONYL CHLORHYDRATE IN A WEIGHT RATIO OF 2:1 ON AN ANHYDROUS BASIS

| | Control | Parts By Weight | | | |
| | | 1 | 2 | 3 | 4 |
|---|---|---|---|---|---|
| Aluminum Chlorhydrate (1) | 31.3 | 43.0 | 40.8 | 38.8 | 36.5 |
| Zirconyl Chlorhydrate (2) | 37.5 | 51.6 | 49.0 | 46.6 | 44.4 |
| Encapsulator G | — | 5.4 | 10.2 | 14.6 | 19.1 |
| Liquid/Gel | G | G | G | G | G/L |
| Time to Gel (Approximate) | 10 Mins. | 30 Mins. | 60 Mins. | 1.5 Hrs. | 4 Hrs. |
| pH of 10% Solution | 4.40 | 3.4 | 3.5 | 3.5 | 3.6 |

(1) 50% aqueous solution.
(2) 20% aqueous solution.

As indicated above in spray drying test Examples 7 and 8, practice of this invention does not interfere with other additives that have been used as buffering agents in the past. To further emphasize this point a broader investigation was undertaken to show that desirable concentrations of the encapsulators even in the presence of other additives, still fall within the broad ranges stated above. Two series of tests were conducted; one using aluminum chlorhydrate and zirconyl chlorhydrate in a ratio of 4:1, and another series at a ratio of 2:1, on an anhydrous basis by weight, in the presence of aminoacetic acid and varying percentages of Encapsulator G. The data from these tests are shown in Tables VII and VIII below:

TABLE VII

EFFECT OF VARIOUS CONCENTRATIONS OF ENCAPSULATOR G IN THE PRESENCE OF AMINOACETIC ACID IN AQUEOUS SOLUTIONS OF ALUMINUM CHLORHYDRATE AND ZIRCONYL CHLORHYDRATE IN A RATIO OF 4:1 ON AN ANHYDROUS BASIS, BY WEIGHT

| | | | Parts By Weight | | | | | | | |
|---|---|---|---|---|---|---|---|---|---|---|
| | Control A | Control B | 1 | 2 | 3 | 4 | 5 | 6 | 7 | 8 |
| Aluminum Chlorhydrate (1) | 59.7 | 59.7 | 59.7 | 57.9 | 55.9 | 54.1 | 52.3 | 50.6 | 49.1 | 47.6 |
| Zirconyl Chlorhydrate (2) | 35.8 | 35.8 | 35.8 | 34.8 | 33.6 | 32.4 | 31.7 | 30.4 | 29.5 | 28.6 |
| Encapsulator G | — | — | 4.5 | 7.3 | 10.5 | 13.5 | 16.3 | 18.9 | 21.4 | 23.8 |
| Aminoacetic Acid | — | 0.1 | 0.0 | 0.1 | 0.1 | 0.1 | 0.1 | 0.1 | 0.1 | 0.1 |
| Liquid/Gel | G | G | G | G | G | G | L | L | L | L |
| Time to Gel (Approximate) | 10 Mins. | 10 Mins. | 30 Mins. | 45 Mins. | 70 Mins. | 80 Mins. | — | — | — | — |
| pH of 10% solution | 3.2 | 3.2 | 3.6 | 3.7 | 3.7 | 3.8 | 3.9 | 4.0 | 4.0 | 4.0 |

(1) 50% aqueous solution.
(2) 20% aqueous solution.

TABLE VIII

EFFECT OF VARIOUS CONCENTRATIONS OF ENCAPSULATOR G IN THE PRESENCE OF AMINOACETIC ACID IN AQUEOUS SOLUTIONS OF ALUMINUM CHLORHYDRATE AND ZIRCONYL CHLORHYDRATE IN A RATIO OF 2:1 ON AN ANHYDROUS BASIS, BY WEIGHT

| | | | Parts By Weight | | | |
|---|---|---|---|---|---|---|
| | Control A | Control B | 1 | 2 | 3 | 4 |
| Aluminum Chlorhydrate (1) | 43.0 | 43.0 | 43.0 | 40.8 | 38.8 | 36.5 |
| Zirconyl Chlorhydrate (2) | 51.6 | 51.6 | 51.6 | 49.0 | 46.6 | 44.4 |
| Encapsulator G | — | — | 5.3 | 10.1 | 14.5 | 19.0 |
| Aminoacetic Acid | — | 0.1 | 0.1 | 0.1 | 0.1 | 0.1 |
| Liquid/Gel | G | G | G | G | G | L |
| Time to Gel (Approximate) | 10 Mins. | 10 Mins. | 50 Mins. | 70 Mins. | 90 Mins. | — |
| pH of 10% solution | 3.1 | 3.1 | 3.1 | 3.4 | 3.5 | 3.6 |

(1) 50% aqueous solution.
(2) 20% aqueous solution.

As noted above, the most efficacious antiperspirant chemicals exhibit a very strong tendency to absorb or pick up water from the atmosphere rapidly. In general, as acidity of these antiperspirant chemicals increases, efficacy also increases with a marked increase of hygroscopicity. It would be a distinct advantage of this tendency to pick up water if it could be extended over a relatively broad time period thus making the antiperspirant effect longer lasting. To illustrate this point, two chambers were prepared each having a different controlled relative humidity as follows:

Chamber A—Relative Humidity 90%
Chamber B—Relative Humidity 20%

Samples of test materials with and without the encapsulators of the invention were exactly weighed in triplicate into tared petri dishes. The open petri dishes containing these samples were then exposed for 24 and 48 hour time periods in each of the two relative humidity chambers. Temperatures throughout the test period were ambient, ranging from 20° to 25° C. The results of these tests, tabulated in Table IX below, indicate that moisture pick-up is at a definitely lower level and extended over a broader period of time when the encapsulator is present than when it is not present.

TABLE IX

| | PERCENTAGE WEIGHT GAIN | | | |
|---|---|---|---|---|
| | 20% Relative Humidity Chamber | | 90% Relative Humidity Chamber | |
| Composition | 24 Hours | 48 Hours | 24 Hours | 48 Hours |
| Example 2 Powder | 1.0% gain | 1.0% gain | 59.0% gain | 59.0% gain |
| Example 2 Powder Minus Encapsulator G | 17.0% gain | 28.0% gain | 90.0% gain | 95.0% gain |
| Example 6 Powder | 0% gain | 2.0% gain | 35.0% gain | 35.0% gain |
| Example 6 Powder Minus Encapsulator G | 6.0% gain | 9.0% gain | 45.0% gain | 51.0% gain |

To illustrate the practical aspects of the invention a number of prototype antiperspirants were formulated using encapsulated antiperspirant chemicals prepared as described above. These toiletry products included a body talc, an aerosol antiperspirant spray, a solid-type or stick antiperspirant, an antiperspirant cream, and a roll-on or ball-dispensing antiperspirant, having the formulations set forth below.

ANTIPERSPIRANT BODY TALC

| Ingredients | Parts By Weight |
|---|---|
| Phase A | |
| Branched Chain Ester oil | 1.00 |
| Perfume | 0.50 |
| Phase B | |
| Talc | 92.25 |
| Magnesium Stearate | 3.00 |
| Trichlorohydroxy Diphenyl Ether | 0.25 |
| Antiperspirant Powder of Example 2 | 3.00 |

Method of Preparation

Phase A

Blend components until uniformly clear.

Phase B

Blend all powdered components in a Patterson-Kelley Twin Shell Blender with a liquid spray head attachment until uniformly mixed.

Follow by spraying Phase A onto powdered blend Phase B and continue mixing until uniform.

ANTIPERSPIRANT AEROSOL

| Ingredients | Parts By Weight |
| --- | --- |
| Isopropyl Myristate | 64 |
| Antiperspirant Powder of Example 5 | 34 |
| Fumed Silica | 1 |
| Perfume | 1 |

Method of Preparation

Mix the above ingredients together at room temperature, using medium speed mechanical agitation, until uniformly blended.

Fill into cans and charge with propellant as shown below:

| Aerosol Filling Formula | Percent By Weight |
| --- | --- |
| Concentrate | 10 |
| Propellant | 90 |

The propellant consists of a mixture of 50 parts of trichlorofluoromethane and 50 parts of dichlorodifluoromethane.

ANTIPERSPIRANT STICK

| | Ingredients | Parts By Weight |
| --- | --- | --- |
| 1. | Antiperspirant Powder of Example 6 | 20.0 |
| 2. | Propylene Glycol | 26.0 |
| 3. | Anhydrous Alcohol | q.s. |
| 4. | Stearic Acid Monoethanolamide | 26.0 |
| 5. | Blended Isopropyl Esters | 11.3 |
| 6. | Anhydrous Alcohol | 14.3 |
| 7. | Isopropyl Myristate | 2.0 |
| 8. | Perfume | 0.4 |

Method of Preparation

1. Blend ingredients 1, 2, and 3 together in an appropriate container at room temperature. Then heat to 70°–75° C. on a hot water bath with constant medium speed mechanical agitation until the blend appears homogeneous;

2. Add ingredient 4 and continue agitation, increasing the temperature to 85°–88° C. until dissolved;

3. Cool batch to 76° C., then add ingredients 5, 6, 7 and 8;

4. Using slow speed mechanical agitation allow batch to cool to 70°–72° C. and pour into molds; and 5. Allow to set 60 minutes at room temperature before demolding.

ANTIPERSPIRANT CREAM

| Ingredients | Parts By Weight |
| --- | --- |
| Phase A | |
| Cetyl Alcohol | 5.60 |
| Commercial Acid Stable Self-Emulsifying mixture of Glycerol and Polyoxyethylene Glycol Stearates | 8.50 |
| Wickenol 535 (Vita-Cos)* grain germ oil | 0.25 |
| Di(2-Ethyl Hexyl) Adipate | 1.00 |
| Phase B | |
| Water (Deionized) | 65.65 |
| Antiperspirant Powder of Example 7 | 18.00 |
| Phase C | |
| Perfume | 1.00 |

*Trademark of Wickhen Products, Inc.

Method of Preparation

1. Heat Phase A to 70° C.
2. Heat Phase B to 72° C.
3. Add Phase B to Phase A using medium agitation.
4. Add Phase C to batch at 50° C.
5. Continue medium agitation and cool to 48° C. Fill into jars.

ROLL-ON ANTIPERSPIRANT

| Ingredients | Parts By Weight |
| --- | --- |
| Phase A | |
| Arlacel 165 (Commercial Acid Stable Self-Emulsifying mixture of Glycerol and Polyoxyethylene Glycol Stearates) | 4.45 |
| Cetyl Alcohol | 1.65 |
| Branched Chain Ester oil | 2.30 |
| Phase B | |
| Dionized Water | 70.60 |
| Polyoxyethylene Sorbitan Monolaurate | 0.25 |
| Antiperspirant Powder of Example 5 | 16.00 |
| Polyoxyl Stearate | 4.60 |
| Phase C | |
| Perfume | 0.15 |

Method of Preparation

1. Heat Phase A to 72° C. in hot water bath.
2. Heat water Phase B to 72° C. in a hot water bath.
3. Add oil Phase A to water Phase B at 72° C. and mix using medium speed mechanical agitation. When temperature drops to 45° C. slowly add perfume (Phase C) and continue mixing and cooling until temperature falls to 35° C.
4. Fill into containers.

While the invention has been described above in conjunction with a number of specific and preferred embodiments thereof, those skilled in the art will recognize that these are merely illustrative of many others and that the invention is to be limited only by the scope of the appended claims and the prior art.

What is claimed is:

1. As a new composition of matter, a dry powder capable of being incorporated into a wide variety of consumer antiperspirant products, which is obtained by drying an aqueous solution of the ingredients and pulverizing the dried product, and which consists essentially of from about 55 to about 90% by weight of active acidic antiperspirant material and about 3 to about 45% by weight of at least partially hydrolyzed carbohydrate derived from natural waxy maize, said hydrolyzed carbohydrate being soluble in water and acting to buffer and encapsulate said acidic antiperspirant.

2. A dry powder antiperspirant composition according to claim 1 in which said hydrolyzed carbohydrate is soluble in water to the extent of at least about 35%, by weight.

3. A composition according to claim 1 wherein the carbohydrate is derived from corn starch.

4. A composition according to claim 3 wherein the carbohydrate is a dextrin.

5. A composition according to claim 3 wherein the carbohydrate is a malto-dextrin.

6. A composition according to claim 3 wherein the carbohydrate is corn syrup solids.

7. A composition according to claim 1 wherein the active acidic antiperspirant contains aluminum.

8. A composition according to claim 7 wherein the active antiperspirant is aluminum chlorhydrate.

9. A composition according to claim 7 wherein the active antiperspirant is aluminum chloride.

10. A composition according to claim 7 wherein the active antiperspirant is aluminum sulfate.

11. A composition according to claim 7 wherein the active antiperspirant is a mixture of aluminum-containing antiperspirants.

12. A composition according to claim 7 wherein the active antiperspirant is aluminum bromohydrate.

13. A composition according to claim 7 wherein the active antiperspirant is aluminum iodohydrate.

14. A composition according to claim 1 wherein the active acidic antiperspirant contains zirconium.

15. A composition according to claim 14 wherein the active antiperspirant is zirconyl chlorhydrate.

16. A composition according to claim 1 wherein the active acidic antiperspirant is a mixture of such materials.

17. A composition of claim 16 wherein the active acidic antiperspirant comprises a mixture of aluminum and zirconium-containing antiperspirants.

18. A composition of claim 16 wherein the active antiperspirant is a mixture of aluminum chlorhydrate and zirconyl chlorhydrate.

19. A composition of claim 1 wherein the carbohydrate is a product derived by drying a high-maltose corn syrup to obtain a powder having a dextrose equivalent of about 34 to 38, a pH in 50% aqueous solution of about 4.8 to 5.2 and a distribution of saccharides of about 6% monosaccharides, about 29% disaccharides, about 11% trisaccharides, about 12% tetrasaccharides and about 42% pentasaccharides and higher polysaccharides.

20. An aqueous solution capable of being dried to form a dry powder antiperspirant material of claim 1, said solution consisting essentially of water, about 25% to about 45% of an active antiperspirant material and about 3% to about 55% by weight of said solution of hydrolyzed carbohydrate.

21. An aqueous solution according to claim 20 wherein the carbohydrate is a dextrin.

22. An aqueous solution according to claim 20 wherein the carbohydrate is a malto-dextrin.

23. An aqueous solution according to claim 20 wherein the carbohydrate is a corn syrup solids.

24. An aqueous solution according to claim 20 wherein the acidic antiperspirant contains a material selected from the group consisting of aluminum-containing antiperspirants, zirconium-containing antiperspirants and mixtures thereof.

25. A method for inhibiting the corrosion of processing equipment in the manufacture of aqueous acidic antiperspirant compositions which comprises dissolving in said aqueous solutions from about 3 to 45% of a water soluble at least partially hydrolyzed carbohydrate derived from natural waxy maize.

26. The method according to claim 25 in which said carbohydrate is soluble in water to the extent of at least 35% by weight.

27. A method for inhibiting the gelation of aqueous solutions of mixed aluminum and zirconium antiperspirant materials which comprises dissolving in said solutions from about 3 to 45% by weight thereof of a water soluble at least partially hydrolyzed carbohydrate derived from natural waxy maize.

28. A consumer antiperspirant product for application to the human body comprising a dry powder antiperspirant composition of claim 1.

29. A consumer antiperspirant product for application to the human body comprising a dry powder antiperspirant composition according to claim 1 consisting essentially of an acidic antiperspirant chemical encapsulated in a material derived from corn syrup which buffers said active antiperspirant to a dermatologically acceptable level and controls the release of active antiperspirant over a prolonged period of time on the human skin.

* * * * *